US010344293B2

United States Patent
An et al.

(10) Patent No.: US 10,344,293 B2
(45) Date of Patent: Jul. 9, 2019

(54) VACCINE COMPOSITION FOR CLASSICAL SWINE FEVER FROM PLANT AND MANUFACTURING METHOD THEREOF

(71) Applicants: BIOAPPLICATIONS INC., Pohang-si, Gyeongsangbuk-do (KR); REPUBLIC OF KOREA (ANIMAL AND PLANT QUARANTINE AGENCY), Gimcheon-si, Gyeongsangbuk-do (KR)

(72) Inventors: Dong Jun An, Anyang-si (KR); Seong In Lim, Anyang-si (KR); Jae Young Song, Anyang-si (KR); Hye Young Jeoung, Anyang-si (KR); Eun Ju Sohn, Pohang-si (KR); In Hwan Hwang, Pohang-si (KR); Nam Jo Park, Gyeongsangbuk-do (KR); Yong Jik Lee, Pohang-si (KR); Nam Hyung Kim, Pohang-si (KR); Sung Min Gu, Pohang-si (KR)

(73) Assignees: BIO APPLICATIONS INC., Pohang-si, Gyeongsangbuk-Do (KR); REPUBLIC OF KOREA (ANIMAL AND PLANT QUARANTINE AGENCY), Gimcheon-si, Gyeongsangbuk-Do (KR)

( * ) Notice: Subject to any disclaimer, the term of this patent is extended or adjusted under 35 U.S.C. 154(b) by 0 days.

(21) Appl. No.: 15/315,233

(22) PCT Filed: May 12, 2016

(86) PCT No.: PCT/KR2016/005037
§ 371 (c)(1),
(2) Date: Jul. 2, 2018

(87) PCT Pub. No.: WO2017/195919
PCT Pub. Date: Nov. 16, 2017

(65) Prior Publication Data
US 2018/0305710 A1    Oct. 25, 2018

(51) Int. Cl.
*C12N 15/82* (2006.01)
*A23K 20/147* (2016.01)
(Continued)

(52) U.S. Cl.
CPC ........ *C12N 15/8258* (2013.01); *A23K 20/142* (2016.05); *A23K 20/147* (2016.05);
(Continued)

(58) Field of Classification Search
None
See application file for complete search history.

(56) References Cited

U.S. PATENT DOCUMENTS

2018/0305710 A1* 10/2018 An ...................... A61K 39/145

OTHER PUBLICATIONS

Daniell et al. (Trends in Plant Science. 14 (12): 669-678).*
(Continued)

*Primary Examiner* — Shanon A. Foley
(74) *Attorney, Agent, or Firm* — Lucas & Mercanti, LLP

(57) ABSTRACT

A recombinant vector for transforming a plant, a plant transformed with the recombinant vector, a plant-made classical swine fever virus antigen pmE2 protein expressed in the plant and uses thereof is provided. By using a recombinant vector having a polynucleotide encoding a GP55 protein of CSFV according to the present invention; and a polynucleotide encoding a cellulose-binding domain protein; and a plant transformed with the recombinant vector, a plant-made classical swine fever virus antigen pmE2 protein may be produced with high efficiency, and has higher safety and stability than those achieved by other production methods. Also, since the plant-derived classical swine fever virus antigen protein pmE2 has a cellulose-binding domain (CBD) protein, it may be usefully used as an (Continued)

effective marker to determine a virus exposure pathway and an antibody producing pathway.

19 Claims, 8 Drawing Sheets

Specification includes a Sequence Listing.

(51) Int. Cl.
    *G01N 33/559*     (2006.01)
    *A61K 39/145*     (2006.01)
    *C07K 14/11*     (2006.01)
    *A61K 39/12*     (2006.01)
    *C07K 14/005*     (2006.01)
    *G01N 33/569*     (2006.01)
    *A23K 20/174*     (2016.01)
    *A23K 20/142*     (2016.01)
    *A23K 50/30*     (2016.01)
    *A61K 39/00*     (2006.01)

(52) U.S. Cl.
    CPC ............ *A23K 20/174* (2016.05); *A23K 50/30* (2016.05); *A61K 39/12* (2013.01); *A61K 39/145* (2013.01); *C07K 14/005* (2013.01); *C07K 14/11* (2013.01); *C12N 15/8205* (2013.01); *C12N 15/8257* (2013.01); *G01N 33/56983* (2013.01); *A61K 2039/517* (2013.01); *C12N 2770/24034* (2013.01); *G01N 2333/183* (2013.01)

(56) References Cited

OTHER PUBLICATIONS

Okay et al. (AIMS Bioengineering. 2018; 5 (3): 151-161).*
Lee et al. (Plant Biotechnology Journal. Jan. 2015; 13: 62-72).*
Alignment of SEQ ID 1 with Geneseq database accession No. AXW71463 by Bae et al in KR2010015187 Feb. 2010.*
Alignment of SEQ ID 2 with Geneseq database accession No. AEF78271 by Bae et al in WO2006011779.*
M.L. Penrith, et al; Classical swine fever (hog cholera): review of aspects relevant to control; Transboundary and emerging diseases; vol. 58; 2011; pp. 187-196.

* cited by examiner

FIG. 1

FIG. 2
Expession and measurement of expression level of classical swine fever virus antigen protein in transformed Arabidopsis thaliana Lane PM : protein size marker
Control protein : Isolated and purified CBD protein
NC: total-extract of wild-type Arabidopsis thaliana
TG-line: total-extract of homozygous line of
transformed Arabidopsis thaliana
PC: total-extract of different Arabidopsis thaliana
expressing CBD protein

FIG. 3

Confirmation of antigenicity of classical swine fever virus antigen protein in transformed Arabidopsis thaliana strong positive/ weak positive/ negative

Kit control

* CSFV-Ag ELISA kit (JenoBiotech)

Diluted-total extract

| | 200 | 400 | 800 | 1600 | 3200 | 6400 |
|---|---|---|---|---|---|---|
| TG-1 | | | | | | |
| TG-2 | | | | | | |
| TG-3 | | | | | | |
| TG-4 | | | | | | |
| TG-5 | | | | | | |
| WT | | | | | | |

*TG: transformed Arabidopsis thaliana line, WT: wild-type Arabidopsis thaliana

FIG. 4

Confirmation of antigenicity of classical swine fever virus antigen protein in transformed Arabidopsis thaliana

PM  NC  TG-line(buf.A) 1 2 3 4 5   NC  TG-line(buf.B) 1 2 3 4 5

66▶
45▶
(kDa)

Immunoblot

66▶
45▶
(kDa)

Membrane Coomassie-stained

* HRPO α-CSFV conjugate (JenoBiotech)

Lane
PM : protein size marker
NC: total-extract of wild-type Arabidopsis thaliana
TG-line: total-extract treated with different buf. A and B

FIG. 7

[ Antibody detection from plant-derived antigen protein-injected mouse ]

α-CSFV IgG (CSFV-Ab ELISA kit, JenoBiotech)

Kit-CT     PBS     Ag+adj.

$10^{-2}$   $10^{-3}$    $10^{-2}$   $10^{-3}$   $10^{-4}$

NC

PC

α-CBD IgG

Kit-CT     PBS     Ag+adj.

[ Antibody detection from plant-derived antigen protein-injected mouse ]
* CSFV-Ab ELISA kit(JenoBiotech)

| Condition | OD 405 nm, Abs. | | | S/P value | | | VNT |
|---|---|---|---|---|---|---|---|
| | $10^{-2}$ | $10^{-3}$ | $10^{-4}$ | $10^{-2}$ | $10^{-3}$ | $10^{-4}$ | |
| PBS | 0.07 | 0.07 | - | < 0 | < 0 | - | < 2 |
| | 0.08 | 0.07 | - | < 0 | < 0 | - | < 2 |
| | 0.07 | 0.07 | - | < 0 | < 0 | - | < 2 |
| Ag+adj. | 0.90 | 0.47 | 0.16 | 0.35 | 0.14 | < 0 | ≥ 512 |
| | 1.01 | 0.86 | 0.44 | 0.40 | 0.33 | 0.12 | ≥ 512 |
| | 1.08 | 0.83 | 0.35 | 0.44 | 0.32 | 0.08 | ≥ 512 |

| Control | NC | PC | CPC |
|---|---|---|---|
| Effective standard | < 0.3 | ≥ 0.5 | ≥ 0.3 |
| Experimental value | 0.19 | 2.22 | 2.03 |

*S/P determination standard: positive ≥ 0.14, negative ≤ 0.14
*Virus neutralization titer

FIG. 9

Confirmation of usability of plant-derived classical swine fever virus antigen protein as marker vaccine

Immunized Mouse

|  | 10⁻² | 10⁻³ |
| --- | --- | --- |
| α-CBD IgG | | |
| α-CSFV IgG | | |
|  | PBS | Plant-Ag |

Kit-control swine

|  | 2x10⁻² | 2x10⁻² |
| --- | --- | --- |
| α-CBD IgG | | |
| α-CSFV IgG | | |
|  | NC | PC |

Field swine: 2x10⁻¹, 2x10⁻², 2x10⁻¹, 2x10⁻², 2x10⁻¹ — α-CBD IgG, α-GP55 IgG, α-CSFV IgG

Antigen
- CBD protein isolated from transformed E. coli
- Antigen protein isolated from plant(GP55)
- Kit-CSFV Ag (CSFV-Ab ELISA kit, JenoBiotech)

Animal serum (Primary antibody)
- Plant-derived antigen protein-injected mouse
- kit-control swine (CSFV-Ab, JenoBiotech)
- Field swine raised in domestic animal farm

FIG. 10

[ Confirmation of usability of plant-derived classical swine fever virus antigen protein as marker vaccine ]

α-GFP IgG: Ag-1, Ag-2, Ag-3

α-CBD IgG: Ag-3, Ag-4

Antigen
1. GFP protein isolated from transformed plant
2. GFP protein isolated from transformed E. coli
3. GFP-CBD protein isolated from transformed E. coli
4. CBD protein isolated from transformed E. coli

Primary antibody
Mouse serum obtained by injection of GFP-CBD protein isolated from transformed E. coli

FIG. 15

| Group | | 27 December, 2013 | | | | | | | | | | |
|---|---|---|---|---|---|---|---|---|---|---|---|---|
| | | 14 days after challenge | | | | | | | | | | |
| | | tonsil | heart | kidney | lung | liver | spleen | small intestine | large intestine | submandibular LN | inguinal region | mesentery |
| Control group | 3 | + | + | + | + | + | + | + | + | + | + | + |
| | 4 | + | + | + | + | + | + | + | + | + | + | + |
| | 5 | + | + | + | + | + | + | + | + | + | + | + |
| | 6 | + | + | + | + | + | + | + | + | + | + | + |
| Experimental groups | 7 (Inoculation, once) | + | - | - | - | - | w(+) | - | - | + | + | + |
| | 8 (Inoculation, once) | + | - | - | - | - | - | - | - | + | - | + |
| | 9 (Inoculation, twice) | + | - | - | - | - | - | - | - | w(+) | w(+) | w(+) |
| | 10 (Inoculation, twice) | - | - | - | - | - | - | - | - | - | - | - |

FIG. 16

| Group | | Before vaccination | 14 days after vaccination | 28 days after vaccination | 3 days after challenge | 5 days after challenge | 7 days after challenge | 10 days after challenge (9, 11) | 14 days after challenge |
|---|---|---|---|---|---|---|---|---|---|
| Control group | 3 | 8 | | | 10 | 4 | <4 | <4 | 10 |
| | 4 | 8 | | | 8 | 10 | <4 | <4 | <4 |
| | 5 | 8 | | | 10 | 4 | <4 | <4 | 4 |
| | 6 | 8 | | | 16 | 8 | <4 | <4 | 8 |
| Experimental groups | 7 (Inoculation, once) | | 10 | 16 | 16 | 32 | 128 | 256 | 512 |
| | 8 (Inoculation, once) | | 4 | 8 | 10 | 32 | 64 | 256 | 512 |
| | 9 (Inoculation, twice) | 16 | 16 | 512 | 512 | 512 | 1024 | 4096 | 4096 |
| | 10 (Inoculation, twice) | <4 | 16 | 2048 | 2048 | 2048 | 4096 | 4096 | 4096 |

VACCINE COMPOSITION FOR CLASSICAL SWINE FEVER FROM PLANT AND MANUFACTURING METHOD THEREOF

CROSS-REFERENCE TO RELATED APPLICATIONS

This application is a 371 of PCT/KR2016/005037, filed May 12, 2016, the contents of which are incorporated herein by reference.

TECHNICAL FIELD

The present invention relates to a recombinant vector for transforming a plant, a plant transformed with the recombinant vector, a plant-made classical swine fever virus antigen plant-made E2 (pmE2) protein expressed in the plant, and uses thereof.

BACKGROUND ART

Classical swine fever is a type of infectious disease, which is a disease caused by a pathogen, that is, classical swine fever virus (CSFV), and does not occur in humans or other animals, but once occurring in pigs, most of the infected pigs are not cured and die (Penrith, M.-L., Vosloo, W. and Mather, C. (2011), Classical Swine Fever (Hog Cholera): Review of Aspects Relevant to Control. Transboundary and Emerging Diseases, 58: 187-196). The classical swine fever, classified as a List A epidemic by the World Organization for Animal Health (OIE), and also classified as a first-class epidemic in Korea by the Law on Domestic Animal Epidemic Prevention, is very contagious to pigs, leading to high fatality, accompanied with a high fever and bleeding, and developed into an acute, subacute, or chronic condition. As mentioned above, since the classical swine fever is an infectious disease with high mortality and morbidity, the prevention thereof is recognized as a critical issue to such an extent that the future of the pig industry cannot be guaranteed without eradication of the classical swine fever. Regarding the classical swine fever, a pig is the only natural host, and spread of the classical swine fever is mainly caused by a virus which is capable of infecting all ages of pigs sensitive to the virus. In Korea, for disease control, vaccination with a live vaccine prepared with a modified live virus, LOM strain, has been carried out. Since a live vaccine for the classical swine fever cannot be serologically distinguished from a wild-type virus, recombinant vaccines such as a marker vaccine are globally in development to differentiate antibodies produced by wild-type virus infection and vaccination. Korea has also focused on development of vaccines for practical use to simply and precisely identify antibodies generated by field infection and antibodies generated by vaccination in terms of the use of a vaccine.

Meanwhile, the remarkable development in molecular biology and genetic engineering techniques is also applied to the field of plants, and thus efforts to produce useful bioactive substances from a plant are being steadily made. The production of useful substances in a plant provides various benefits as follows: 1) extraordinary reduction in a production cost; 2) complete elimination of various contaminants (a virus, an oncogene, an enterotoxin, etc.) that may be generated in a popular method in the art (for isolating and purifying a protein following synthesis in animal cells or microorganisms); 3) seed stock management by seeds even in a commercialization stage, unlike animal cells or microorganisms; and 4) supply of the corresponding substance according to an increased demand within the shortest time because, when the demand for the corresponding substance is rapidly increased, the plant system of the present invention is absolutely preferable to the conventional animal cell system in terms of engineering technology or costs required for mass production.

The reason that the method for producing a useful substance from a plant transformed as described above has received attention is a protein synthesis pathway of a plant. Post-translational modification is the key process of the protein synthesis in a mammal, and since the plant has a protein synthesis pathway of a eukaryotic organism, it can produce a very similar protein to a protein expressed in a mammal. However, despite the several benefits mentioned above, techniques for obtaining useful bioactive substances (medically useful proteins, vaccines and industrially valuable enzymes, etc.) from a plant with high efficiency have not yet had much success.

DISCLOSURE

Technical Problem

The inventors have conducted studies to improve low efficiency in protein production using a plant, thereby constructing a recombinant vector comprising a polynucleotide encoding a GP55 protein of classical swine fever virus; and a polynucleotide encoding a cellulose-binding domain (CBD) protein, and found that the use of a transformed plant transformed with the recombinant vector may result in the production of a plant-derived classical swine fever virus antigen pmE2 protein with high efficiency, and exhibit higher safety and stability than other production methods. Also, they also found that the pmE2 protein is useable as a marker for determining a virus exposure pathway and an antibody producing pathway, and thus the present invention was completed.

An object of the present invention is to provide a recombinant vector for producing a plant-derived classical swine fever virus antigen pmE2 protein.

Another object of the present invention is to provide a transformed plant for producing a plant-derived classical swine fever virus antigen pmE2 protein transformed with the recombinant vector.

Still another object of the present invention is to provide a plant-derived classical swine fever virus antigen pmE2 protein expressed in the transformed plant, and a method for producing the same.

Yet another object of the present invention is to provide a vaccine, pharmaceutical or feed composition for preventing classical swine fever comprising the recombinant protein as an active ingredient.

Yet another object of the present invention is to provide a composition and kit for diagnosing classical swine fever virus comprising the recombinant protein.

Yet another object of the present invention is to provide a method for preventing classical swine fever by administering the vaccine composition to an animal.

Yet another object of the present invention is to provide a method for detecting CSFV using the recombinant protein and a method for determining an antibody producing pathway of the CSFV.

Technical Solution

To achieve the above-mentioned objects, the present invention provides a recombinant vector for producing a plant-derived classical swine fever virus antigen pmE2 protein, which comprises a polynucleotide encoding a GP55 protein of CSFV; and a polynucleotide encoding a cellulose-binding domain protein.

Also, the present invention provides a transformed plant for producing a plant-derived classical swine fever virus antigen pmE2 protein transformed with the recombinant vector.

The present invention further provides a plant-derived classical swine fever virus antigen pmE2 protein expressed in the transformed plant.

The present invention further provides a method for producing a plant-derived classical swine fever virus antigen pmE2 protein, which comprises (a) transforming *Agrobacterium* with the recombinant vector; (b) introducing the transformed *Agrobacterium* into a plant; and (c) isolating and purifying a plant-derived classical swine fever virus antigen pmE2 protein expressed in the plant.

The present invention further provides a vaccine, pharmaceutical or feed composition for preventing classical swine fever comprising the recombinant protein as an active ingredient.

The present invention further provides a composition and kit for diagnosing CSFV comprising the recombinant protein.

The present invention further provides a method for preventing classical swine fever by administering the vaccine composition to an animal.

The present invention further provides a method for detecting CSFV by detecting CSFV from a sample through an antigen-antibody reaction using the recombinant protein.

The present invention further provides a method for detecting a CSFV antibody producing pathway, which comprises: 1) administering the vaccine composition to an experimental subject, and extracting blood from the experimental subject; 2) isolating serum from the blood extracted in step 1); and 3) treating the serum isolated in step 2) with the plant-derived classical swine fever virus antigen pmE2 protein as an antigen to induce a reaction.

Advantageous Effects

By using a recombinant vector comprising a polynucleotide encoding a GP55 protein of CSFV according to the present invention; and a polynucleotide encoding a cellulose-binding domain protein; and a plant transformed with the recombinant vector, a plant-made classical swine fever virus antigen pmE2 protein can be produced with high efficiency, and has higher safety and stability than those achieved by other production methods. Also, since the plant-derived classical swine fever virus antigen protein pmE2 comprises a cellulose-binding domain (CBD) protein, it can be usefully used as an effective marker to determine a virus exposure pathway and an antibody producing pathway.

DESCRIPTION OF DRAWINGS

FIG. 1 illustrates a map of a recombinant vector for producing a plant-derived classical swine fever virus antigen pmE2 protein.

FIG. 2 illustrates the expression of a pmE2:CBD protein in a transformed plant which is assessed by western blotting.

FIG. 3 illustrates antigenicity of a protein expressed in a transformed plant, which is assessed by ELISA.

FIG. 4 illustrates antigenicity of a protein expressed in a transformed plant, which is assessed by western blotting.

FIG. 7 illustrates production of a specific antibody against CSFV and a specific antibody against a CBD protein comprising a plant-derived classical swine fever virus antigen protein pmE2 in serum obtained, after the plant-derived classical swine fever virus antigen protein pmE2 is administered.

FIG. 8 illustrates antibody titers measured in mice to which the plant-derived classical swine fever virus antigen protein pmE2 is administered.

FIG. 9 illustrates an infection route of CSFV using a plant-derived classical swine fever virus antigen protein pmE2.

FIG. 10 illustrates usability of a plant-derived classical swine fever virus antigen protein pmE2 in determination of the viral infection route according to reactions between different antigens and immunized mouse serum.

FIG. 15 illustrates antigen detection after autopsies on animal models (pigs) after challenge.

FIG. 16 illustrates an examination result of protective antibody titers of animal models (pigs) after challenge.

MODES OF THE INVENTION

Figure 5:
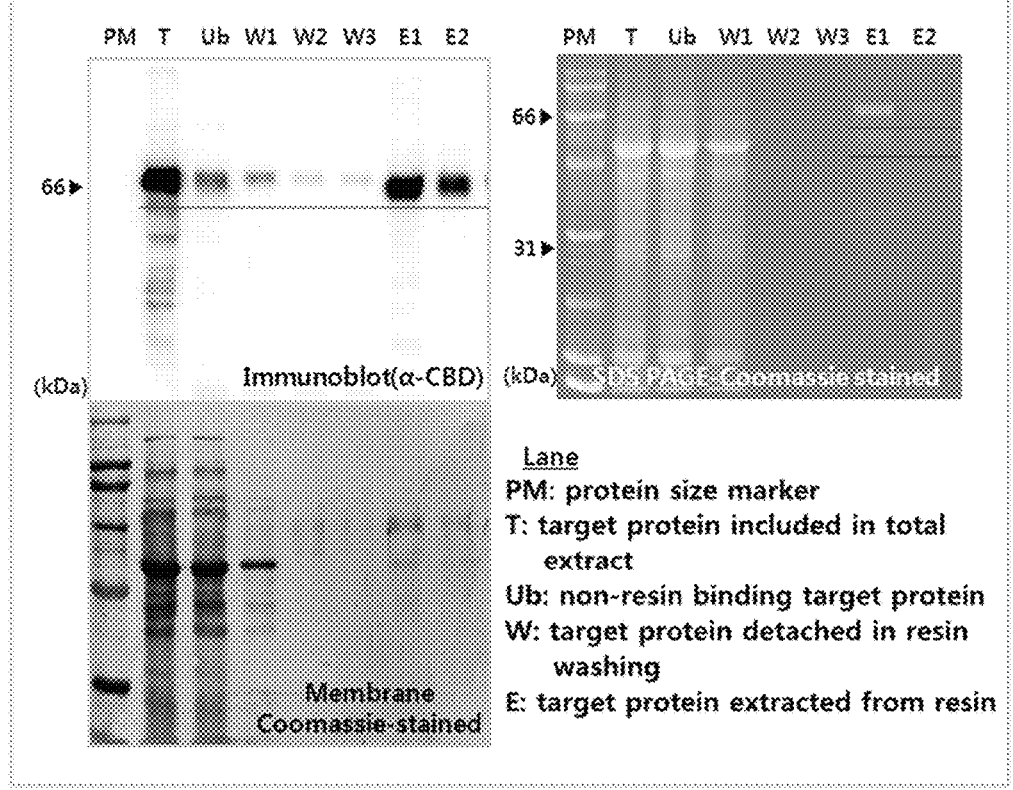
FIG. 5 illustrates a plant-derived classical swine fever virus antigen protein pmE2 isolated and purified from a transformed plant.

The present invention provides a recombinant vector for producing a plant-derived classical swine fever virus antigen pmE2 protein, which comprises a polynucleotide encoding a GP55 protein of CSFV; and a polynucleotide encoding a CBD protein.

The term "expression vector" used herein refers to a plasmid, virus or a different vehicle known in the art, into which a gene or polynucleotide may be inserted or introduced. The polynucleotide according to the present invention may be operably linked to an expression control sequence, and the operably-linked polynucleotide may be included in one expression vector comprising a selective marker and a replication origin. The term "operably linked" may indicate a gene and an expression control sequence, which is linked to enable gene expression when a suitable molecule is bound to the expression control sequence. The term "expression control sequence" refers to a DNA sequence controlling the expression of a polynucleotide sequence operably linked in a specific host cell. Such a control sequence comprises a promoter for transcription, a random operator sequence for controlling transcription, a sequence encoding a proper mRNA ribosome-binding site, and sequences for controlling termination of transcription and translation.

The term "Classical swine fever virus (CSFV)" used herein is an enveloped single stranded RNA virus in the genus of Pestivirus, which has an antigen-determining site (epitope) on a type of envelope-associated glycoprotein (E proteins) with a size of approximately 12.3~12.5 kb, called an E2 glycoprotein. For this reason, the E2 protein is considered a relatively important structural protein. The E2 protein of CSFV is known to cause virus neutralization, and to play an important role in an immunologically protective mechanism of the classical swine fever.

The polynucleotide encoding the GP55 protein of CSFV may be set forth in SEQ ID NO: 1, and the polynucleotide encoding the CBD protein may be set forth in SEQ ID NO: 2, but the present invention is not limited thereto.

The recombinant vector may comprise one or more selected from the group consisting of a CaMV 35S promoter; a 5' untranslational region (UTR) gene of M17; a polynucleotide encoding a chaperone binding protein (BiP); and a polynucleotide encoding a His-Asp-Glu-Leu (HDEL) (SEQ ID NO: 6) protein.

The 5' UTR(M17) may comprise the base sequence of SEQ ID NO: 3, and the nucleotide encoding the BiP protein may be represented by a base sequence of SEQ ID NO: 4, but the present invention is not limited thereto.

The vector may be represented by the following vector map, comprising the base sequence of SEQ ID NO: 5, but the present invention is not limited thereto.

In the present invention, the polynucleotides or genes comprising the base sequences of SEQ ID NOs: 1 to 5 may be artificially synthesized using a nucleic acid synthesizer with reference to the base sequence of the corresponding gene, or may be prepared by PCR with oligonucleotides as primers, which have complementary sequences for both ends of a target polynucleotide or gene, using genomic DNA or each gene of CSFV as a template. Meanwhile, due to degeneracy of codons, the nucleotides or genes of the present invention may be present in various base sequences, all of which are encompassed in the scope of the present invention. Also, variants comprising the base sequences of SEQ ID NOs: 1 to 5 are encompassed in the scope of the present invention. Specifically, the nucleotides or genes of the present invention may comprise the base sequence having a 70% or more, preferably 80% or more, more preferably 90% or more, and most preferably 95% or more sequence homology with the base sequences of SEQ ID NOs: 1 to 5. The term "sequence homology (%)" with respect to a polynucleotide is confirmed by comparing two optimally arranged sequences with a comparison region, and a part of the polynucleotide sequence in the comparison region may be added or deleted (i.e., a gap), compared with the reference sequence (without addition or deletion) with respect to the optimal arrangement of the both sequences.

In the present invention, the GP55 protein is one of the E2 antigen domains of CSFV, and the 5' UTR(M17) may be used to increase an amount of a synthesized protein, and the BiP protein may be used to translocate a target protein to the N-terminal endoplasmic reticulum using a genomic DNA sequence. In addition, as the CBD protein may be used as a hybrid protein tag, and the HDEL protein assists a protein to remain in the endoplasmic reticulum, folding and assembly mediated by molecular chaperones may be increased and thus proteolysis may further be reduced. Therefore, the CBD protein and the HDEL protein may be used in combination to accumulate a final target protein in the endoplasmic reticulum.

As the vectors, binary vectors such as pCHF3, pPZP, pGA and pCAMBIA-series vectors are preferably used, and in one exemplary embodiment of the present invention, a pBI121 vector was used, but the present invention is not limited thereto.

Also, the present invention provides a plant transformed with the recombinant vector.

A method of introducing the recombinant vector of the present invention to a plant may be, but is not limited to, an *Agrobacterium* sp.-mediated method, particle gun bombardment, silicon carbide whiskers, sonication, electroporation, or precipitation using polyethylene glycol (PEG). In one embodiment of the present invention, the recombinant vector of the present invention was introduced to a plant, for example, *Arabidopsis thaliana*, by the *Agrobacterium* sp.-mediated method.

In the present invention, the plant transformed with the recombinant vector may be obtained by a conventional method in the art such as a sexual propagation method or asexual propagation method. More specifically, the plant of the present invention may be obtained by sexual propagation including production of seeds through the pollination of flowers and propagation from the seeds. Also, following the transformation of the plant with the recombinant vector of the present invention, the plant of the present invention may be obtained by an asexual method including callus induction, rooting and soil acclimation according to a conventional method. That is, an explant of the plant transformed with the recombinant vector in the present invention was plated in a suitable medium known in the art, cultured under proper conditions to induce callus formation, and then, after shoot formation, it is transferred to and cultured in a hormone-free medium. Two weeks later, the shoot is transferred to a rooting medium to induce a root. After the root is induced, it may be planted in soil and then acclimated, thereby obtaining the plant according to the present invention. The transformed plant in the present invention may include tissue, cells or seeds, which are obtained therefrom.

In the present invention, the plant may be a dicotyledon or monocotyledon, and the dicotyledon may be, but is not limited to, *Arabidopsis thaliana*, soybean, tobacco, eggplant, pepper, potato, tomato, Chinese cabbage, white radish, cabbage, lettuce, peach, pear, strawberry, watermelon, oriental melon, cucumber, carrot and celery, and the monocotyledon may be, but is not limited to, rice, barley, wheat, rye, corn, sugar cane, oat and onion.

Also, the present invention provides a plant-derived classical swine fever virus antigen pmE2 protein expressed in the transformed plant.

The plant-derived classical swine fever virus antigen pmE2 protein according to the present invention is a fusion of the GP55 protein of CSFV and the CBD protein, but the present invention is not limited thereto.

In the present invention, the plant-derived classical swine fever virus antigen pmE2 protein includes proteins having a wild-type amino acid sequence and an amino acid sequence variant thereof. The variant of the plant-derived classical swine fever virus antigen pmE2 protein refers to a protein having different sequences due to deletion, insertion, nonconservative or conservative substitution of one or more amino acid residues, or a combination thereof. Amino acid exchange in a protein and a peptide, which does not overall alter the activity of a molecule is known in the art. The plant-derived classical swine fever virus antigen pmE2 protein or a variant thereof may be extracted or synthesized from nature or may be prepared by a gene recombination method based on a DNA sequence.

Also, the present invention provides a method for producing a plant-derived classical swine fever virus antigen pmE2 protein, which comprises: (a) transforming *Agrobacterium* with a recombinant vector; (b) introducing the transformed *Agrobacterium* to a plant; and (c) isolating and purifying a plant-derived classical swine fever virus antigen pmE2 protein expressed in the plant.

The plant may be one or more plant bodies selected from the group consisting of *Arabidopsis thaliana*, wheat, barley, corn, bean, potato, red bean, oat, sorghum, rice, Chinese cabbage, white radish, pepper, strawberry, tomato, watermelon, cucumber, cabbage, oriental melon, pumpkin, Welsh onion, onion, carrot, ginseng, tobacco, cotton, sesame, sugar cane, beet, perilla, peanut, rape, apple tree, pear tree, jujube tree, peach, kiwifruit, grape, tangerine, persimmon, plum, apricot, banana, rose, gladiolus, gerbera, carnation, chrysanthemum, lily, tulip, ryegrass, red clover, orchard grass, alfalfa, tall fescue and perennial ryegrass, and preferably *Arabidopsis thaliana*, but the present invention is not limited thereto.

In the present invention, the isolation and purification method in step (c) may employ a known method suitable for physical and chemical properties of the corresponding material, for example, amorphous cellulose (AMC), distillation, electrodialysis, pervaporation, chromatography, solvent extraction, reactive extraction, or HPLC, and preferably, AMC, but the present invention is not limited thereto.

In one exemplary embodiment of the present invention, a recombinant vector comprising a polynucleotide encoding the GP55 protein of CSFV; a polynucleotide encoding a CBD protein; a CaMV 35S promoter; a 5' UTR(M17); a polynucleotide encoding a BiP protein; and a polynucleotide encoding a HDEL protein was prepared. After the prepared recombinant vector was transformed into *Arabidopsis thaliana* using *Agrobacterium*, the transformed plant was cultured to fuse the GP55 protein of CSFV and the CBD protein, and the plant-derived classical swine fever virus antigen pmE2 protein was obtained through isolation and purification. It was confirmed that the plant-derived classical swine fever virus antigen pmE2 protein was expressed in the transformed plant at a high level to enable mass production, and had immunity with respect to the CSFV and the highest titer, which showed that it has a virus neutralizing effect. Also, depending on the detection of the CBD protein included in the pmE2 protein, the plant-derived classical swine fever virus antigen pmE2 protein was identified as a marker for determining a virus exposure pathway. In addition, when an animal model was inoculated with the pmE2 protein, it was confirmed that the pmE2 protein is effective for preventing the CSFV, inhibits virus amplification and propagation, and has an excellent defensive capability.

Also, the present invention provides a vaccine or pharmaceutical composition for preventing classical swine fever, which comprises the recombinant protein as an active ingredient.

The term "vaccine" used herein refers to a biological agent containing an antigenic substance providing immunity to the body, and an immunogen generating immune responses in an organism through introduction or injection into a living organism so as to prevent classical swine fever.

The vaccine composition of the present invention may further comprise an adjuvant in addition to the recombinant protein. The adjuvant may be any one known in the art without limitation, and the vaccine composition may further comprise, for example, complete or incomplete forms of Freund's adjuvant to increase its immunity.

The vaccine or pharmaceutical composition according to the present invention may be prepared as a formulation in which an active ingredient is incorporated in a pharmaceutically acceptable carrier. Here, the pharmaceutically acceptable carrier is a carrier, an excipient or a diluent, which is conventionally used in the pharmaceutical field. Examples of the pharmaceutically acceptable carriers used in the vaccine or pharmaceutical composition of the present invention may include, but are not limited to, lactose, dextrose, sucrose, sorbitol, mannitol, xylitol, erythritol, maltitol, starch, acacia gum, alginate, gelatin, calcium phosphate, calcium silicate, cellulose, methyl cellulose, polyvinyl pyrrolidone, water, methylhydroxybenzoate, propylhydroxybenzoate, talc, magnesium stearate and mineral oil.

The vaccine or pharmaceutical composition of the present invention may be used in dosage forms including an oral form such as powder, a granule, a tablet, a capsule, a suspension, an emulsion, a syrup, or an aerosol, a drug for external use, a suppository, or a sterilized injectable solution according to a conventional method suitable for each form.

The vaccine or pharmaceutical composition of the present invention may be formulated with a filler, a thickening agent, a binder, a wetting agent, a dispersant, a diluent such as a surfactant or an excipient, which is conventionally used. A solid formulation for oral administration may be a tablet, pill, powder, granule or capsule, and such a solid formulation may be prepared by mixing at least one of excipients, for example, starch, calcium carbonate, sucrose, lactose and gelatin, with the active ingredient. Also, in addition to the simple excipient, lubricants such as magnesium stearate and talc may also be used. As a liquid formulation for oral administration, a suspension, a liquid for internal use, an emulsion, or a syrup may be used, and as well as a generally-used diluent such as water or liquid paraffin, various types of excipients, for example, a wetting agent, a sweeter, a fragrance and a preservative may be included. A formulation for parenteral administration includes a sterilized aqueous solution, a non-aqueous solvent, a suspension, an emulsion, a lyophilizing agent and a suppository. As the non-aqueous solvent or suspension, propylene glycol, polyethylene glycol, a vegetable oil such as olive oil, or an injectable ester such as ethyl oleate may be used. As a suppository base, Witepsol, Tween 61, cacao butter, laurin fat, or glycerogelatin may be used.

The vaccine or pharmaceutical composition according to the present invention may be administered to an individual by various routes. Administration may be carried out by any of the predictable methods, for example, oral, intravenous, intramuscular, subcutaneous, and intraperitoneal injections.

Taking into account the age, body weight, sex and physical condition of an individual, a dose of the vaccine or pharmaceutical composition according to the present invention is selected. A dose necessary for inducing a protective immune response in an individual without particular side effects may vary according to the presence of an excipient and a recombinant protein as an immunogen. Generally, the vaccine or pharmaceutical composition of the present invention contains 0.1 to 1000 µg, and preferably 0.1 to 100 µg of the protein per ml of the sterilized solution in the recombinant protein of the present invention. For the vaccine composition, following the initial content, randomly repeated antigen stimulations may be carried out as needed.

Also, the present invention provides a feed composition for preventing classical swine fever, which comprises the recombinant protein as an active ingredient.

The feed includes corn, rice, common rice straw, wild grass, soilage, ensilage, dry grass, native grass as well as byproducts such as pork, beef and chicken, but the present invention is not limited thereto, and any type of feed used in livestock farming is usable. A method for blending the recombinant protein of the present invention with such feed after addition of these components may be mechanical mixing, adsorption or occlusion, but the present invention is not limited thereto.

Also, the present invention provides a composition for diagnosing CSFV, which comprises the recombinant protein.

Also, the present invention provides a kit for diagnosing CSFV, which comprises the recombinant protein.

The kit for diagnosis may be manufactured to comprise a reaction solution as needed, which may be easily accomplished using a known technique. The kit of the present invention may further comprise a reagent required for CSFV diagnosis, which may be, but is not limited to, a buffer. Also, the kit may comprise an instruction manual. The instruction manual is printed text describing how to use the kit, for example, a method for preparing a buffer, and presented reaction conditions. The instructions include a brochure in the form of a pamphlet or leaflet, a label adhered to the kit, and descriptions on the surface of a package including the kit. Also, the instruction manual includes information disclosed or provided by electrical media such as the Internet.

Also, the present invention provides a method for preventing classical swine fever by administering the vaccine composition to an animal.

The animal is preferably a mammal, and more preferably a pig.

Also, the present invention provides a method for detecting CSFV by detecting CSFV from a sample through an antigen-antibody reaction using the recombinant protein.

The antigen-antibody reaction may be detected by one or more methods selected from the group consisting of tissue immunostaining, radioimmunoassay (RIA), enzyme-linked immunosorbent assay (ELISA), western blotting, immunoprecipitation assay, immunodiffusion assay, complement fixation assay, fluorescence-activated cell sorter (FACS) and protein chip assay, but the present invention is not limited thereto.

The sample may be one or more selected from the group consisting of cells, blood, urine, saliva and tissue, but the present invention is not limited thereto.

Also, the present invention provides a method for determining an antibody producing pathway of CSFV, which comprises:

1) administering the vaccine composition to an experimental subject, followed by extracting blood from the experimental subject; 2) isolating the serum from the blood extracted in step 1); and 3) treating the serum isolated in step 2) with the plant-derived classical swine fever virus antigen pmE2 protein as an antigen to induce a reaction.

In the reaction in step 3), when antibodies for both of the GP55 protein of CSFV and the (CBD) protein are detected, it can be determined that the antibodies formed in the experimental subject are produced by administration of the vaccine composition. Also, when the antibody for the GP55 protein of CSFV is only detected in the reaction of step 3), it can be determined that the antibody is produced by infection of CSFV.

Hereinafter, to help in understanding the present invention, exemplary examples will be provided. However, the following examples are merely provided to more easily understand the present invention, and the scope of the present invention is not limited to the following examples.

EXAMPLE 1

Construction of Recombinant Vector Comprising GP55 Gene of Classical Swine Fever Virus In order to construct a recombinant vector having a GP55 gene of a classical swine fever virus to produce a classical swine fever virus antigen protein in a plant with high efficiency, the following experiment was performed.

More specifically, as shown in FIG. 1, a recombinant vector in which a CaMV 35S promoter; 5' UTR(M17) (SEQ ID NO: 3); a nucleotide sequence a chaperone binding protein (BiP) protein (SEQ ID NO: 4); a nucleotide sequence the GP55 protein (SEQ ID NO: 1); a nucleotide sequence a CBD protein (SEQ ID NO: 2); and a nucleotide sequence a His-Asp-Glu-Leu (HDEL) protein are contained in a pBI121 vector was constructed.

The GP55 protein is one of the E2 antigen domains of CSFV, the 5' UTR(M17) was used to increase an amount of a synthesized protein, and the BiP protein was used to translocate a target protein to an N-terminal endoplasmic reticulum using a genomic DNA sequence. In addition, as the CBD protein was used as a hybrid protein tag, and the HDEL protein assisted a protein to remain in the endoplasmic reticulum, folding and assembly mediated by molecular chaperones were increased and thus proteolysis was further reduced. Therefore, the CBD protein and the HDEL protein were used in combination to accumulate a final target protein in the endoplasmic reticulum. The base sequence of the constructed recombinant vector was set forth in SEQ ID NO: 5.

EXAMPLE 2

Preparation of Transformed Plant Expressing Fusion Protein Comprising Antigenic GP55 Protein of CSFV and CBD protein To prepare a transformed plant expressing a recombinant fusion protein comprising an antigenic GP55 protein of CSFV and a CBD protein, the following experiment was performed.

More specifically, *Arabidopsis thaliana* expressing the recombinant fusion protein comprising the GP55 protein of CSFV and the CBD protein was prepared by an *Agrobacterium*-mediated transforming method for the recombinant vector constructed in Example 1. Since the recombinant vector of Example 1 has resistance to kanamycin in a plant, following the selection of the transgenic *Arabidopsis thaliana*, a kanamycin resistance test and western blotting using an antibody for CBD were performed to confirm expression of the recombinant fusion protein. Also, expression of a target protein in *Arabidopsis thaliana* and quantification of an expression level are shown in FIG. 2.

As shown in FIG. 2, it was confirmed that the CBD protein was expressed in the transformed *Arabidopsis thaliana* through western blotting, and thereby the GP55 protein of CSFV fused with the CBD protein was also expressed.

EXAMPLE 3

Confirmation of Antigenicity of GP55 Protein of CSFV Prepared in Transformed Plant To confirm antigenicity of the GP55 protein of CSFV in the recombinant fusion protein comprising the antigenic GP55 protein of CSFV and the CBD protein, derived from the transformed plant prepared in Example 2, the following experiment was performed.

More specifically, homozygous seeds with stable expression of a target protein were ultimately ensured through generation advance of the transformed plant prepared in Example 2, an expression level of the target protein was quantified for each seed line to determine the line to be used in the experiment. The seeds of the determined line were cultured to obtain a plant, a protein was extracted using an extraction buffer commonly used in protein extraction for ELISA. Antigenicity of the GP55 protein of CSFV in the fusion protein of the antigenic GP55 protein and the CBD protein, derived from the transformed plant prepared in Example 2, was confirmed using a kit for clinical diagnosis (Jeno Biotech Inc. (now, Median Diagnostics), a CSFV-Ag ELISA kit) used in CSFA antigen detection, and the ELISA result and the western blotting result are shown in FIGS. 3 and 4, respectively.

As shown in FIGS. 3 and 4, it was confirmed that the plant-derived protein prepared in the present invention shows high reactivity to commercially-available antibodies for clinical diagnosis in both of the ELISA and the western blotting. Therefore, it was confirmed that the recombinant fusion protein comprising the antigenic GP55 protein of CSFV and the CBD protein, derived from the transformed plant prepared in Example 2, the GP55 protein of CSFV has antigenicity. Also, it was confirmed that the GP55 protein of CSFV was expressed in the transformed plant at a high level, thereby enabling mass-production.

EXAMPLE 4

Isolation And Purification Of Plant-derived Classic Swine Fever Antigen Protein pmE2 From Transformed Plant 4-1. Isolation and Rurification of Recombinant Fusion Protein Since the transformed plant prepared in the present invention was prepared to also express the CBD protein, proteins was isolated and purified with high efficiency using cellulose. Here, as a resin for the isolation and purification of a target protein, amorphous cellulose (AMC) specially prepared as microcrystalline cellulose (MCC) was used.

4-2. Identification of Fractions of Isolated and Purified Recombinant Proteins

The recombinant proteins isolated and purified according to Example 4-1 were identified by two methods. For the first method, the presence of the GP55 protein of CSFV as a target protein was confirmed by western blotting. In the isolated and purified protein, the CBD protein was fused with the target protein, which is the GP55 protein of CSFV, and thus the reaction with respect to the CBD protein used as a primary antibody indirectly indicates the presence of the GP55 protein of CSFV. Here, to confirm problems in the isolation and purification processes by relatively comparing degrees of distribution of the GP55 protein of CSFV in fractions of a plant solution containing the protein, the fractions were loaded in respective wells of a gel with equal ratios, and the result is shown in FIG. 5. For the second method, as shown in FIG. 5, a protein band was identified from the SDS-PAGE gel through Coomassie staining for the fractions, and the overall pattern was compared with the Coomassie stained-western blotting result. The result is shown in FIG. 5.

As shown in FIG. 5, according to the western blotting result, it was confirmed that a considerable amount of the GP55 protein is bound to a resin. Also, it was confirmed that a small amount remains in the Ub lane. In the E1 and E2 lanes, it was confirmed that a trace amount of the protein was lost after washing three times, but most of the protein was recovered. When the recovered protein was confirmed by SDS-PAGE, the clear GP55 protein band was visually identified, and non-specific bands were not identified, which indicates a high purity.

4-3. Quantification of Isolated and Purified Proteins

Figure 6:
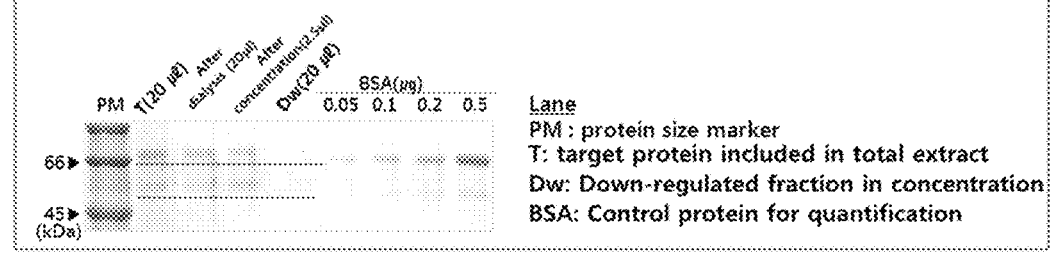
FIG. 6 illustrates a quantification result of the plant-derived classical swine fever virus antigen protein pmE2 isolated and purified from a transformed plant.

To purify the protein solution isolated in 4-1 once more, the protein solution was dialyzed in PBS. Afterwards, the resulting solution was concentrated using a centrifugal filter tube, and treated by Coomassie staining on a SDS-PAGE gel, and the result is shown in FIG. 6. With reference to a certain concentration of a bovine serum albumin (BSA) solution, concentrations of the protein bands were compared, and a target protein (including the CBD protein) was quantified. Here, an isolated protein solution (before dialysis), a protein solution after dialysis, a protein solution after concentration and a solution at a decreased concentration (capable of confirming the loss of proteins) were loaded individually and then quantified together to provide accuracy for reconfirming purification and quantification. The result is shown in FIG. 6.

As shown in FIG. 6, it was confirmed that buffer exchange is possible without protein loss even following the dialysis, and the final vaccine material, such as a protein antigen, was able to be prepared at a desired concentration through concentration, and then quantified, compared with the reference protein.

Accordingly, the recombinant fusion protein comprising the antigenic GP55 protein of CSFV and the CBD protein expressed in the transformed plant was called "plant-made E2(pmE2)."

EXAMPLE 5

Confirmation of Immunogenicity and Virus Neutralization Activity of Plant-derived Classic Swine Fever Antigen Protein pmE2 in Animal Model To confirm whether the plant-derived classical swine fever virus antigen protein pmE2 has immunogenicity and a virus neutralization activity by inducing antibodies in an animal model, the following experiment was performed.

More specifically, the plant-derived classical swine fever virus antigen protein pmE2 protein was administered to the animal model, mice. The negative control mice were treated with PBS, and treated groups were treated with a combination of an antigen mixed with a Freund's adjuvant at equal amounts three times in two weeks, and then the serum was extracted from each group. The production of a specific antibody against the administered antigen was detected using an antibody kit for clinical diagnosis for CSFV (Jeno Biotech (now, Median Diagnostics), CSFV-Ab ELISA kit). The result of scoring according to the kit manual is shown in FIG. 7. Also, virus neutralization activity in the same mouse serum analyzed by the Animal and Plant Quarantine Agency is shown in FIG. 8.

As shown in FIG. 7, it was confirmed that antibody titers are recorded as positive values in all treated groups, which indicates that the plant-derived classical swine fever virus antigen protein pmE2 prepared by the method of the present invention has immunogenicity against CSFV in mice.

Also, as shown in FIG. 8, it was confirmed that all treated groups show very high titers.

Therefore, it was confirmed that the plant-derived classical swine fever virus antigen protein pmE2 prepared according to the present invention produces specific antibodies in mice, and the antibodies have high titers with respect to virus neutralization activity.

EXAMPLE 6

Confirmation of Usability of Plant-derived Classical Swine Fever Virus Antigen Protein pmE2 as Marker for Determining CSFV Exposing Pathway Since the CBD protein is fused in the plant-derived classical swine fever virus antigen protein pmE2 (a recombinant fusion protein comprising the antigenic GP55 protein of CSFV and the CBD protein), to confirm the usability of the CBD protein as a marker for determining a virus exposure pathway, the following experiment was performed.

More specifically, ELISA using the CBD proteins including the plant-derived classical swine fever virus antigen protein pmE2 as antigens was used to measure specific antibodies against the antigens from the following sera. Specific antibodies for the CBD protein included in the plant-derived classical swine fever virus antigen protein pmE2 were detected from the control (swine) sera included in a kit for clinical diagnosis (Jeno Biotech (now, Median Diagnostics) CSFV-Ab ELISA kit), sera of 7 sows and 28 piglets, raised in an animal farm, and mouse sera extracted in Example 5. For target sows, ages at the time of blood collection and the latest classical swine fever vaccination time could not be confirmed, and for target piglets, ages at the time of the blood collection were approximately three weeks old, and vaccination could not be confirmed. The results of confirming the usability of the plant-derived classical swine fever virus antigen protein pmE2 as a marker for determining a CSFV exposing pathway is shown in FIG. 9.

As shown in FIG. 9, from the serum of the mouse exposed to the plant-derived protein, a specific antibody against the CBD protein included in the plant-derived classical swine fever virus antigen protein pmE2 was also detected. On the other hand, in all experimental subjects, the control sera included in the kit and the sera of the raised sows and piglets showed specific antibodies against CSFV, which were detected as positive values of titers according to the kit manual, but specific antibodies against the CBD proteins were not detected. Here, while origins of the specific antibodies against CSFV detected from the sows and piglets had not been identified, specific antibodies against the CBD protein were not detected, which indicated that the CSFV was not related to the protein used in the present invention.

Therefore, it was confirmed that the plant-derived classical swine fever virus antigen protein pmE2 of the present invention was fully qualified to be used as a marker for determining a virus exposure pathway.

Also, it was intended to confirm whether the CBD protein included in the plant-derived classical swine fever virus antigen protein pmE2 of the present invention generally causes immune responses to produce specific antibodies. If the CBD protein is a common protein that can produce antibodies, the production of the CBD antibodies for pmE2 can increase reliability to positively verify the production of CSFV antibodies and pmE2 antibodies due to wild-type virus infection. To confirm such assumption, a protein in which a green fluorescent protein (GFP) is fused with the CBD protein was obtained from transgenic $E.\ coli$, and used as an antigen for injection into a mouse, and then specific antibodies against GFP and CBD were identified from sera obtained by injection of the fusion protein as an antigen into mice through ELISA. Here, several proteins derived from different origins as an antigen were tested.

As shown in FIG. 10, as the mouse serum injected with $E.\ coli$-derived GFP-CBD showed increased optical densities with respect to various GFP proteins, it showed that α-GFP IgG was easily produced, and α-CBD IgG against various types of CBD proteins were also produced with high titers.

Therefore, it was confirmed that the CBD proteins co-fused in the plant-derived classical swine fever virus antigen protein pmE2 of the present invention produce each type of specific antibody regardless of the type of target protein. Also, the plant-derived classical swine fever virus antigen protein pmE2 (the recombinant fusion protein comprising the antigenic GP55 protein of CSFV and the CBD protein) comprises an antigenic GP55 protein of CSFV, which may be used as an antigen. Since the plant-derived classical swine fever virus antigen protein pmE2 also comprises the CBD protein, specific antibodies against the CBD protein can be used to detect infection, and also used to define a virus exposure pathway in an animal as vaccination or natural infection.

EXAMPLE 7

Confirmation of Defensive Capability of Plant-derived Classical Swine Fever Virus Antigen Protein pmE2 in Target Animal (Pig)

7-1. Inoculation of Target Animal (Pig) with Plant-derived Classical Swine Fever Virus Antigen Protein pmE2

To confirm the defensive capability of a plant-derived classical swine fever virus antigen protein pmE2 in a pig animal model, the following experiment was performed.

Figures 11, 12:
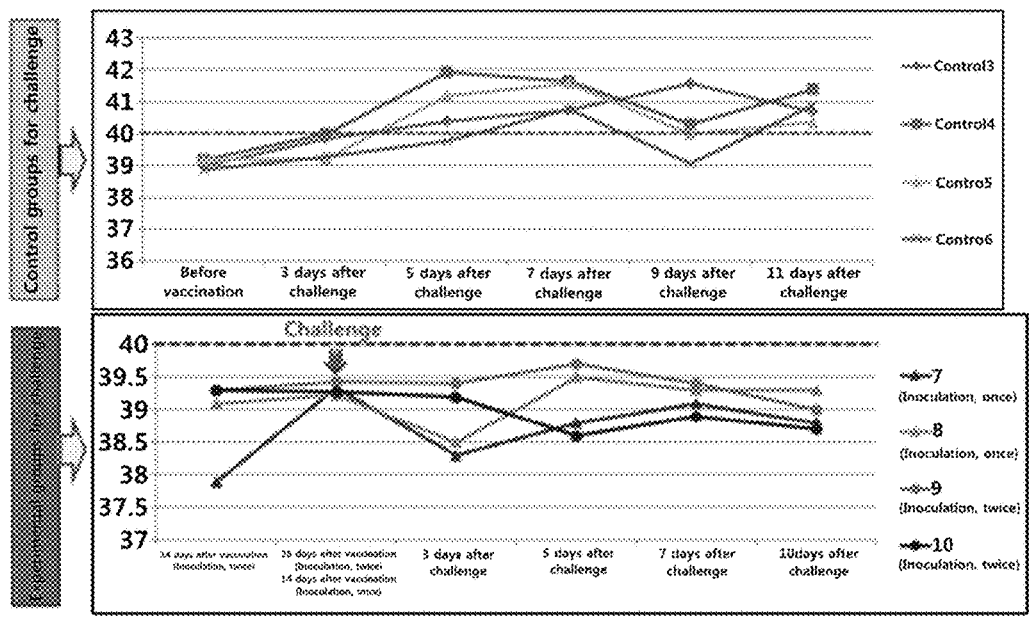
FIG. 11 illustrates a schematic process of an experiment for the defensive capability of a plant-expressed protein.
FIG. 12 illustrates the change in body temperature of animal models (pigs) after challenge.

More specifically, as shown in FIG. 11, eight classical swine fever antibody-negative pigs were selected to be used in an experiment. Among them, four pigs were used as a control group that was not vaccinated with the plant-derived classical swine fever virus antigen protein pmE2, and as experimental groups, one in which each of two pigs was vaccinated once with 100 μg of the plant-derived classical swine fever virus antigen protein pmE2 and one in which each of the remaining two pigs was vaccinated twice in two weeks with 100 μg of the plant-derived classical swine fever virus antigen protein pmE2 were used. To investigate the shielding from the wild-type virus, a wild-type CSFV (Yeoncheon strain: isolated from Korean wild boars in 2012) was inoculated in a concentration of 10^6.0 TCID 50/ml. Challenge was performed, 14 days after the inoculation, with the plant-derived classical swine fever virus antigen protein pmE2. Two weeks later, the experiment was terminated, and then the animals were killed for autopsy.

7-2. Monitoring of Clinical Symptoms of Pigs After Challenge

It was investigated whether pigs inoculated with the plant-derived classical swine fever virus antigen protein pmE2 had a high fever, which is a typical symptom of febrile diseases, following the challenge with a wild-type strain. The result is show in FIG. 12.

As shown in FIG. 12, it was confirmed that the four pigs of the control group, which were not inoculated with the pmE2 protein of the present invention, began to have an elevated body temperature at 3 days after challenge, had a body temperature elevated to over 40 degrees after 7 days, and maintained such high fever until 11 days. On the other hand, in all of the pigs inoculated with the pmE2 protein of the present invention once or twice, the body temperature was not elevated, but maintained below 40 degrees during 10 days after challenge.

Also, when the pigs were infected by CSFV, the white blood cell level was generally decreased below 9000, and therefore an experiment described below was carried out to investigate whether the reduction in white blood cell level is inhibited by the inoculation with the pmE2 of the present invention. The result is shown in FIG. 13.

Figures 13, 14:
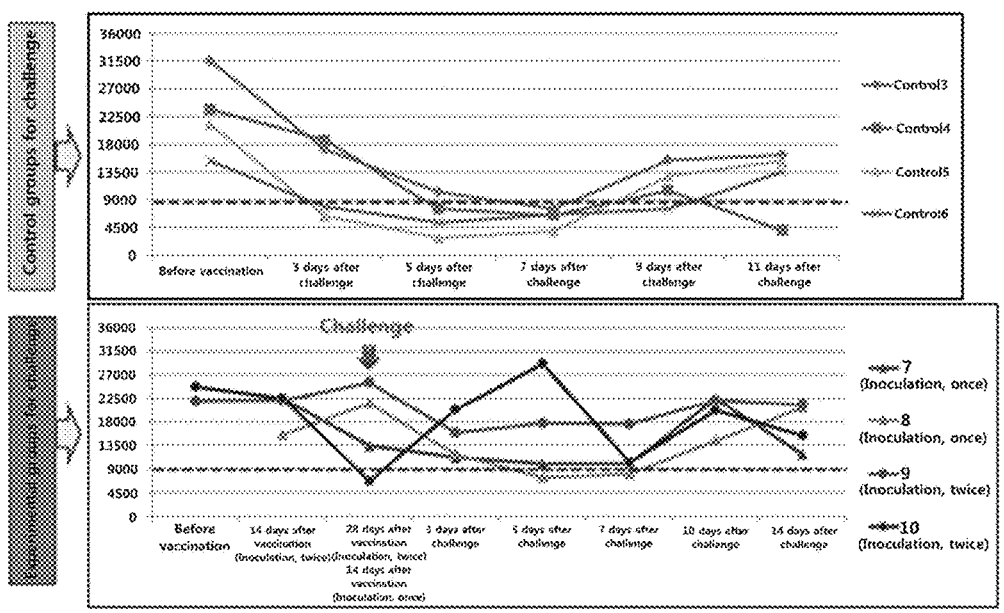
FIG. 13 illustrates the change in white blood cell level in animal models (pigs) after challenge.
FIG. 14 illustrates antigen detection after collection of blood and other samples from animal models (pigs) after challenge.

As shown in FIG. 13, the four pigs of the control group exhibited a decrease in the white blood cell level from three days after challenge, and on day 7, the white blood cell levels of all of the four pigs were decreased below 9000. On the other hand, while the pigs injected with the pmE2 of the present invention have individual differences, it was confirmed that, 10 days after challenge, the white blood cell levels of all pigs were maintained over 9000.

Therefore, it was confirmed that the vaccinated individuals did not show classical swine fever-related clinical symptoms, and according to the inoculation with the pmE2 protein of the present invention, it was effective for protecting against CSFV.

7-3. Monitoring of Antigen Detection from Blood and Specimens of Pigs After Challenge To confirm the inhibition of virus propagation by the pmE2 protein of the present invention after challenge, and antigen detection from blood and samples of the pigs, the following experiment was performed.

More specifically, 3, 5, 7 and 10 days after challenge, whole blood, rhinorrhea, saliva and feces of the pigs of the control and experimental groups were sampled, and wild-type strain virus antigens were detected by PCR. PCR was conducted to amplify the 5'NCR region (421 bp) under conditions of 30 min/42° C., 15 min/94° C., (40 cycles: 30 sec/94° C., 30 sec/55° C., 45 sec/72° C.), and 5 min/72° C. The result is shown in FIG. 14.

As shown in FIG. 14, on day 3 after challenge, in the pigs of the control group, antigens were detected from the whole blood, and on day 5, antigens were also detected from the rhinorrhea, saliva and feces. On the other hand, in the pigs inoculated with the pmE2 vaccine of the present invention once, antigens were not detected from the rhinorrhea and saliva, but antigens were detected from the whole blood, and many samples showed weak-positive responses. Also, no antigen was detected from one of the pigs inoculated with the pmE2 vaccine of the present invention twice, examined from three to 10 days after challenge, and in the other pig, weak antigen responses were shown from the feces on day 3, the whole blood on day 5, and the rhinorrhea on day 7, after challenge.

Therefore, it was confirmed that, due to the treatment with pmE2 protein of the present invention, in vivo virus amplification and propagation were inhibited.

7-4. Investigation of Antigen Detection in Pig Organs After Challenge 14 days after challenge, the pigs of the controls and experimental groups were killed for autopsy, and subjected to PCR to detect the challenged wild-type strain virus antigens in various organs, thereby investigating the influence of the pmE2 protein of the present invention on virus amplification in pig organs. The result is shown in FIG. 15.

As shown in FIG. 15, in the pigs of the control group, the challenged virus antigens were detected from all of a tonsil, the heart, kidney, lung, liver, spleen, small intestine, large intestine, submandibular lymph node, inguinal region and mesentery, and in the pigs injected with the pmE2 protein of the present invention once, virus antigens were detected from the tonsil, submandibular lymph node and mesentery, but not detected from the heart, kidney, lung, liver, small intestine and large intestine. Also, in one of the pigs injected with the pmE2 protein of the present invention twice, antigens were detected from the tonsil, and weak-positive responses were shown from submandibular lymph node, inguinal region, and mesentery, but from all of the organs of the other pig, antigens were not detected.

Therefore, it was seen that the pmE2 vaccine of the present invention was able to protect the pigs from viral attack, and had a dose-dependent effect.

7-5. Confirmation of Antibody Titer Against Plant-Derived Classical Swine Fever Virus Antigen Protein pmE2

The key indicator representing the preventability of the classical swine fever vaccine, which is a protective antibody titer, was investigated, and the result is shown in FIG. 16.

As shown in FIG. 16, it was seen that, in the control group, the antibody titers were no more than 10 before and after challenge, but in the pigs injected with the plant-derived classical swine fever virus antigen protein pmE2 of the present invention, antibody titers were dramatically increased after challenge with the wild-type strain virus. It was estimated that antibodies capable of neutralizing a fever virus were previously memorized by the pmE2 of the present invention, and then boosted by the virus challenge. Also, in the pigs inoculated with the pmE2 protein of the present invention once, protective antibody titers were 16 and 8, respectively, before challenge, and then 5 days after challenge, the titers were 32. Afterward, 14 days after challenge, the titers were 512. It was confirmed that, in the two pigs inoculated with the pmE2 vaccine twice, 14 days after the vaccination, the titers were 16, 28 days after the vaccination, high protective antibody titers of 512 and 2048, respectively, were shown, and after the vaccination, the antibody titers were further increased to be 4096.

Therefore, clinically, when the protective antibody titer is 32 or more, it is considered to have a defensive capability. In this regard, it was demonstrated that the plant-derived classical swine fever virus antigen protein pmE2 of the present invention has an excellent ability to protect against CSFV in pigs.

Hereinafter, preparation examples of the pharmaceutical and feed compositions of the present invention will be described, but these examples are not intended to limit the present invention, but to explain it concretely.

PREPARATION EXAMPLE 1

Preparation of Pharmaceutical Composition 1-1. Preparation of Powder

| | |
|---|---|
| Plant-derived classical swine fever virus antigen protein pmE2 | 20 mg |
| Lactose | 100 mg |
| Talc | 10 mg |

Powder was prepared by mixing the above components and filling the mixture in a sealed pouch.

1-2. Preparation of Tablet

| | |
|---|---|
| Plant-derived classical swine fever virus antigen protein pmE2 | 10 mg |
| Corn starch | 100 mg |

-continued

| Lactose | 100 mg |
|---|---|
| Magnesium stearate | 2 mg |

A tablet was prepared by mixing the above components, and compressing the mixture with a punch.

1-3. Preparation of Capsule

| plant-derived classical swine fever virus antigen protein pmE2 | 10 mg |
|---|---|
| Crystalline cellulose | 3 mg |
| Lactose | 14.8 mg |
| Magnesium stearate | 0.2 mg |

A capsule was prepared by mixing the above components and filling the mixture in a gelatin capsule according to a conventional method for preparing a capsule.

1-4. Preparation of Injection

| plant-derived classical swine fever virus antigen protein pmE2 | 10 mg |
|---|---|
| Mannitol | 180 mg |
| Sterilized distilled water for injection | 2974 mg |
| Na$_2$HPO$_4$2H$_2$O | 26 mg |

An injection was prepared with above component contents per ampoule (2 ml) according to a conventional method for preparing an injection.

1-5. Preparation of Liquid Medicine

| plant-derived classical swine fever virus antigen protein pmE2 | 20 mg |
|---|---|
| Isomerose | 10 g |
| Mannitol | 5 g |
| Distilled water | q.s. |

A liquid medicine was prepared by dissolving the above components in distilled water, adding a suitable amount of a lemon flavoring to be mixed with the above mixture, adding distilled water to the mixture to adjust a total volume to 100 ml, and filling the resulting solution in a brown bottle and then sterilizing the bottle according to a conventional method for preparing a liquid.

PREPARATION EXAMPLE 2

Preparation of Feed Composition

| plant-derived classical swine fever virus antigen protein pmE2 | 100 mg |
|---|---|
| Vitamin E | 0.7 mg |
| L-carnitine | 0.7 mg |

Feed was prepared by mixing the above components according to a conventional method for preparing feed.

The invention claimed is:

1. A recombinant vector for producing a plant-derived classical swine fever virus antigen pmE2 protein, comprising:
   a polynucleotide encoding a GP55 protein of classical swine fever virus (CSFV); and
   a polynucleotide encoding a cellulose-binding domain (CBD) protein,
   wherein the recombinant vector comprises the base sequence of SEQ ID NO: 5.

2. The recombinant vector of claim 1, wherein the polynucleotide encoding the GP55 protein of CSFV is represented by SEQ ID NO: 1.

3. The recombinant vector of claim 1, wherein the polynucleotide encoding the CBD protein is represented by SEQ ID NO: 2.

4. The recombinant vector of claim 1, wherein the recombinant vector includes one or more selected from the group consisting of a CaMV 35S promoter; a 5'untranslational region (UTR) gene of M17; a polynucleotide encoding a chaperone binding protein (BiP) protein; and a polynucleotide encoding a His-Asp-Glu-Leu (HDEL) (SEQ ID NO: 6) protein.

5. The recombinant vector of claim 1, wherein the recombinant vector comprises:
   a CaMV 35S promoter;
   a 5'UTR gene of M17;
   a polynucleotide encoding a chaperone binding protein (BiP) protein;
   a polynucleotide encoding a GP55 protein of CSFV;
   a polynucleotide encoding a cellulose binding domain (CBD) protein;
   a polynucleotide encoding HDEL (SEQ ID NO: 6) protein; and
   a NOS terminator.

6. A transformed plant for producing a plant-derived classical swine fever virus antigen plant-made E2 (pmE2) protein, which is transformed with the recombinant vector of claim 1.

7. A plant-derived classical swine fever virus antigen pmE2 protein, which is expressed in the transformed plant of claim 6.

8. The pmE2 protein of claim 7, wherein the plant-derived classical swine fever virus antigen pmE2 protein comprises a fusion of a GP55 protein of CSFV and a cellulose-binding domain (CBD) protein.

9. A composition for preventing classical swine fever, comprising:
   the plant-derived classical swine fever virus antigen pmE2 protein of claim 7 as an active ingredient.

10. A vaccine composition for preventing classical swine fever, comprising:
    the plant-derived classical swine fever virus antigen pmE2 protein of claim 7 as an active ingredient.

11. A method for preventing classical swine fever, comprising:
    administering the vaccine composition of claim 10 to an animal.

12. A method for determining an antibody producing pathway of classical swine fever virus (CSFV), comprising:
    1) administering of the vaccine composition of claim 10 to an experimental subject and then collecting blood from the experimental subject;
    2) isolating the serum from the blood collected in step 1); and
    3) treating the serum isolated in step 2) with the plant-derived classical swine fever virus antigen pmE2 protein as an antigen to induce a reaction and detecting the antibody-antigen complex.

13. The method of claim 12, wherein, in the reaction of step 3), when antibodies against the GP55 protein of CSFV and the cellulose-binding domain (CBD) protein are detected together, the antibodies formed in the experimental subject are determined to have been produced by the administration of the vaccine.

14. The method of claim 12, wherein, in the reaction of step 3), when only antibodies against the GP55 protein of CSFV are detected, they are determined to have been produced by infection with CSFV.

15. A classical swine fever virus (CSFV) diagnosis kit, comprising:
    the plant-derived classical swine fever virus antigen pmE2 protein of claim 7.

16. A method for detecting classical swine fever virus (CSFV), comprising:
    detecting the CSFV in a sample through an antigen-antibody reaction using the plant-derived classical swine fever virus antigen pmE2 protein of claim 7.

17. The method of claim 16, wherein the antigen-antibody reaction is detected using one or more methods selected from the group consisting of tissue immunostaining, radioimmunoassay (RIA), enzyme-linked immunosorbent assay (ELISA), western blotting, immunoprecipitation assay, immunodiffusion assay, complement fixation assay, fluorescence-activated cell sorter (FACS) and protein chip assay.

18. A method for producing a plant-derived classical swine fever virus antigen pmE2 protein, comprising:
    (a) transforming *Agrobacterium* with the recombinant vector of claim 1;
    (b) introducing the transformed *Agrobacterium* to a plant; and
    (c) isolating and purifying a plant-derived classical swine fever virus antigen pmE2 protein, expressed in the plant.

19. The method of claim 18, wherein the plant is *Arabidopsis thaliana*.

* * * * *

```
                        SEQUENCE LISTING

<160> NUMBER OF SEQ ID NOS: 6

<210> SEQ ID NO 1
<211> LENGTH: 1026
<212> TYPE: DNA
<213> ORGANISM: Artificial Sequence
<220> FEATURE:
<223> OTHER INFORMATION: DNA sequence for gp55 of Classical swine fever
      virus

<400> SEQUENCE: 1
aacggctagc ctgcaaggaa gattacaggt acgcaatatc atcaaccaat gagatagggc        60 tactcgggc cggaggtctc accaccacct ggaaagaata caaccacgat ttgcaactga       120
atgacgggac cgttaaggcc atttgcgtgg caggttcctt taaagtcaca gcacttaatg       180
tggtcagtag gaggtatttg gcatcattgc ataaggaggc tttacccact tccgtgacat       240
tcgagctcct gttcgacggg accaacccat caactgagga aatgggagat gacttcgggt       300
tcgggctgtg cccgtttgat acgagtcctg ttgtcaaagg aaagtacaat acaaccttgt       360
tgaacggtag tgctttctat cttgtctgtc caatagggtg gacgggtgtt atagagtgca       420
cagcagtgag cccaacaact ctgagaacag aagtggtaaa gaccttcagg agggacaagc       480
cctttccgca cagaatggat tgtgtgacca caacagtgga aaatgaagat ttattctact       540
gtaagttggg gggcaactgg acatgtgtga aaggtgaacc agtggtctac acgggggggc       600
tagtaaaaca atgcagatgg tgtggctttg acttcaatga gcctgacgga ctcccacact       660
accccatagg taagtgcatt ttggcaaatg agacaggtta cagaatagtg gattcaacag       720
actgtaacag agatggtgtt gtaatcagca cagaggggag tcatgagtgc ttgatcggta       780
acacgactgt caaggtgcat gcatcagatg aaagactggg ccccatgcca tgcagaccta       840
```

| | |
|---|---|
| aagagatcgt ctctagtgca ggacctgtaa ggaaaacttc ctgtacattc aactacgcaa | 900 |
| aaactttgaa gaacaagtac tatgagccca gggacagcta cttccagcaa tatatgctta | 960 |
| agggcgagta tcagtactgg tttgacctgg acgtgactga ccgccactca gattacttcg | 1020 |
| cagaag | 1026 |

<210> SEQ ID NO 2
<211> LENGTH: 429
<212> TYPE: DNA
<213> ORGANISM: Artificial Sequence
<220> FEATURE:
<223> OTHER INFORMATION: DNA sequence for cellulose-binding domain

<400> SEQUENCE: 2

| | |
|---|---|
| tttcgaagtt caccagtgcc tgcacctggt gataacacaa gagacgcata ttctatcatt | 60 |
| caggccgagg attatgacag cagttatggt cccaaccttc aaatctttag cttaccaggt | 120 |
| ggtggcagcg ccattggcta tattgaaaat ggttattcca ctacctataa aaatattgat | 180 |
| tttggtgacg gcgcaacgtc cgtaacagca agagtagcta cccagaatgc tactaccatt | 240 |
| caggtaagat tgggaagtcc atcgggtaca ttacttggaa caatttacgt ggggtccaca | 300 |
| ggaagctttg atacttatag gatgtatcc gctaccatta gtaatactgc gggtgtaaaa | 360 |
| gatattgttc ttgtattctc aggtcctgtt aatgttgact ggtttgtatt ctcaaaatca | 420 |
| ggaacttct | 429 |

<210> SEQ ID NO 3
<211> LENGTH: 21
<212> TYPE: DNA
<213> ORGANISM: Artificial Sequence
<220> FEATURE:
<223> OTHER INFORMATION: 5'UTR of M17 gene

<400> SEQUENCE: 3

| | |
|---|---|
| ggcgtgtgtg tgtgttaaag a | 21 |

<210> SEQ ID NO 4
<211> LENGTH: 273
<212> TYPE: DNA
<213> ORGANISM: Artificial Sequence
<220> FEATURE:
<223> OTHER INFORMATION: DNA sequence for chapherone binding protein (BiP)

<400> SEQUENCE: 4

| | |
|---|---|
| atggctcgct cgtttggagc taacagtacc gttgtgttgg cgatcatctt cttcggtgag | 60 |
| tgatttccg atcttcttct ccgatttaga tctcctctac attgttgctt aatctcagaa | 120 |
| cctttttcg ttgttcctgg atctgaatgt gtttgtttgc aatttcacga tcttaaaagg | 180 |
| ttagatctcg attggtattg acgattggaa tctttacgat ttcaggatgt ttatttgcgt | 240 |
| tgtcctctgc aatagaagag gctacgaagt taa | 273 |

<210> SEQ ID NO 5
<211> LENGTH: 1862
<212> TYPE: DNA
<213> ORGANISM: Artificial Sequence
<220> FEATURE:
<223> OTHER INFORMATION: particle sequence of recombinant vector

<400> SEQUENCE: 5

| | |
|---|---|
| tctagaggcg tgtgtgtgtg ttaaagaatg gctcgctcgt ttggagctaa cagtaccgtt | 60 |

```
gtgttggcga tcatcttctt cggtgagtga ttttccgatc ttcttctccg atttagatct    120
cctctacatt gttgcttaat ctcagaacct tttttcgttg ttcctggatc tgaatgtgtt    180
tgtttgcaat ttcacgatct taaaaggtta gatctcgatt ggtattgacg attggaatct    240
ttacgatttc aggatgttta tttgcgttgt cctctgcaat agaagaggct acgaagttaa    300
ggatccaacg gctagcctgc aaggaagatt acaggtacgc aatatcatca accaatgaga    360
tagggctact cggggccgga ggtctcacca ccacctggaa agaatacaac cacgatttgc    420
aactgaatga cgggaccgtt aaggccattt gcgtggcagg ttcctttaaa gtcacagcac    480
ttaatgtggt cagtaggagg tatttggcat cattgcataa ggaggcttta cccacttccg    540
tgacattcga gctcctgttc gacgggacca acccatcaac tgaggaaatg ggagatgact    600
tcgggttcgg gctgtgcccg tttgatacga gtcctgttgt caaggaaagt acaatacaa    660 ccttgttgaa cggtagtgct ttctatcttg tctgtccaat agggtggacg ggtgttatag    720
agtgcacagc agtgagccca acaactctga aacagaagtt ggtaaagacc ttcaggaggg    780
acaagccctt tccgcacaga atggattgtg tgaccacaac agtggaaaat gaagatttat    840
tctactgtaa gttggggggc aactggacat gtgtgaaagg tgaaccagtg gtctacacgg    900
gggggctagt aaaacaatgc agatggtgtg ctttgacttc aatgagcctg acggactcc    960 cacactaccc cataggtaag tgcatttttgg caaatgagac aggttacaga atagtggatt   1020
caacagactg taacagagat ggtgttgtaa tcagcacaga ggggagtcat gagtgcttga   1080
tcggtaacac gactgtcaag gtgcatgcat cagatgaaag actgggcccc atgccatgca   1140
gacctaaaga gatcgtctct agtgcaggac ctgtaaggaa aacttcctgt acattcaact   1200
acgcaaaaac tttgaagaac aagtactatg agcccaggga cagctacttc cagcaatata   1260
tgcttaaggg cgagtatcag tactggtttg acctggacgt gactgaccgc cactcagatt   1320
acttcgcaga atcccgggca gattacgaca ttccaacaac tgatgcagag aatttgtatt   1380
ttcagggtcg ggcacaccac caccaccacc actttcgaag ttcaccagtg cctgcacctg   1440
gtgataacac aagagacgca tattctatca ttcaggccga ggattatgac agcagttatg   1500
gtcccaacct tcaaatcttt agcttaccag gtggtggcag cgccattggc tatattgaaa   1560
atggttattc cactacctat aaaaatattg attttggtga cggcgcaacg tccgtaacag   1620
caagagtagc tacccagaat gctactacca ttcaggtaag attgggaagt ccatcgggta   1680
cattacttgg aacaatttac gtggggtcca caggaagctt tgatacttat agggatgtat   1740
ccgctaccat tagtaatact gcgggtgtaa aagatattgt tcttgtattc tcaggtcctg   1800
ttaatgttga ctggtttgta ttctcaaaat caggaacttc tcacgatgag ctctagctcg   1860
ag                                                                  1862

<210> SEQ ID NO 6
<211> LENGTH: 4
<212> TYPE: PRT
<213> ORGANISM: Artificial Sequence
<220> FEATURE:
<223> OTHER INFORMATION: ER retention signal protein

<400> SEQUENCE: 6

His Asp Glu Leu
1
```